United States Patent [19]

Kreissl

[11] Patent Number: 4,563,065
[45] Date of Patent: Jan. 7, 1986

[54] PROTECTIVE GLASSES WITH TEAR-OFF LENSES

[75] Inventor: Franz Kreissl, Traun, Austria

[73] Assignee: Optyl Eyewear Fashion International Corporation, Norwood, N.J.

[21] Appl. No.: 559,788

[22] Filed: Dec. 9, 1983

[30] Foreign Application Priority Data

Mar. 29, 1983 [DE] Fed. Rep. of Germany ....... 3311456

[51] Int. Cl.[4] .......................... G02C 1/00; G02C 7/08
[52] U.S. Cl. ....................................... 351/86; 351/57; 351/47
[58] Field of Search ....................... 351/41, 47, 57, 58, 351/158, 86; 2/434, 429, 438, 441, 443

[56] References Cited

U.S. PATENT DOCUMENTS 4,455,689 6/1984 Boyer ...................................... 2/434

*Primary Examiner*—Rodney B. Bovernick
*Attorney, Agent, or Firm*—Fitch, Even, Tabin & Flannery

[57] ABSTRACT

The protective glasses with tear-off lenses described consist of an eyeglass body with a fixedly mounted main viewing lens and a frame extending essentially around the entire inner extent of the eyeglass body and at a certain spacing in front of the main viewing lens, with a packet of tear off lenses with gripping tabs inserted behind this frame. The gripping tabs of all of the tear-off lenses are attached on the lower edge of the associated lens and on one side of the glasses (that is, right or left) and specifically, via a stem, the other end is attached foldable by means of a hinge to the associated tear-off lens, whereby, in the case of an inserted packet of tear-off lenses, the individual stems are folded up about their hinges and the stem of one lens is held fast in this folded-up position by means of the lens lying over it, or, in front of it.

7 Claims, 10 Drawing Figures

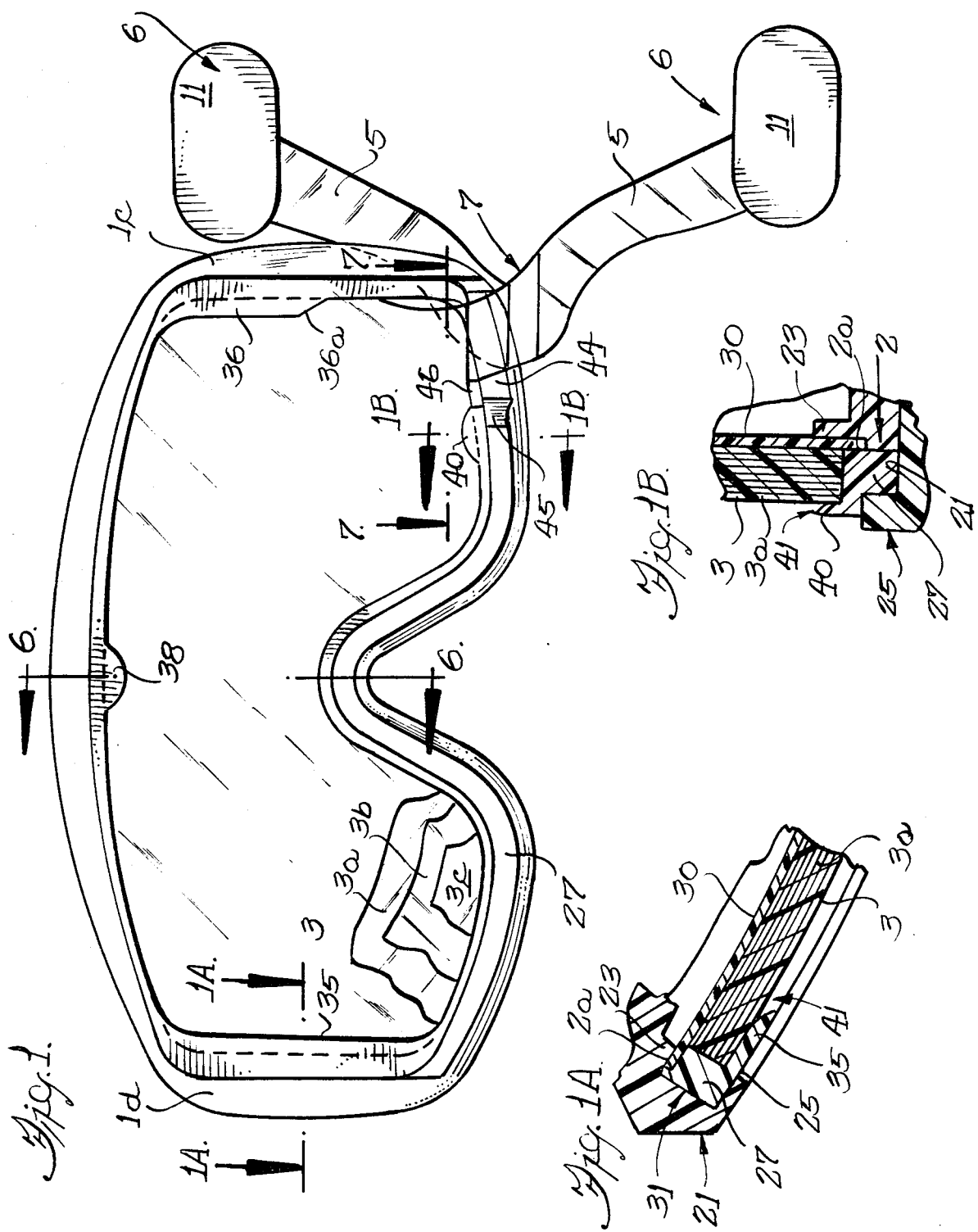

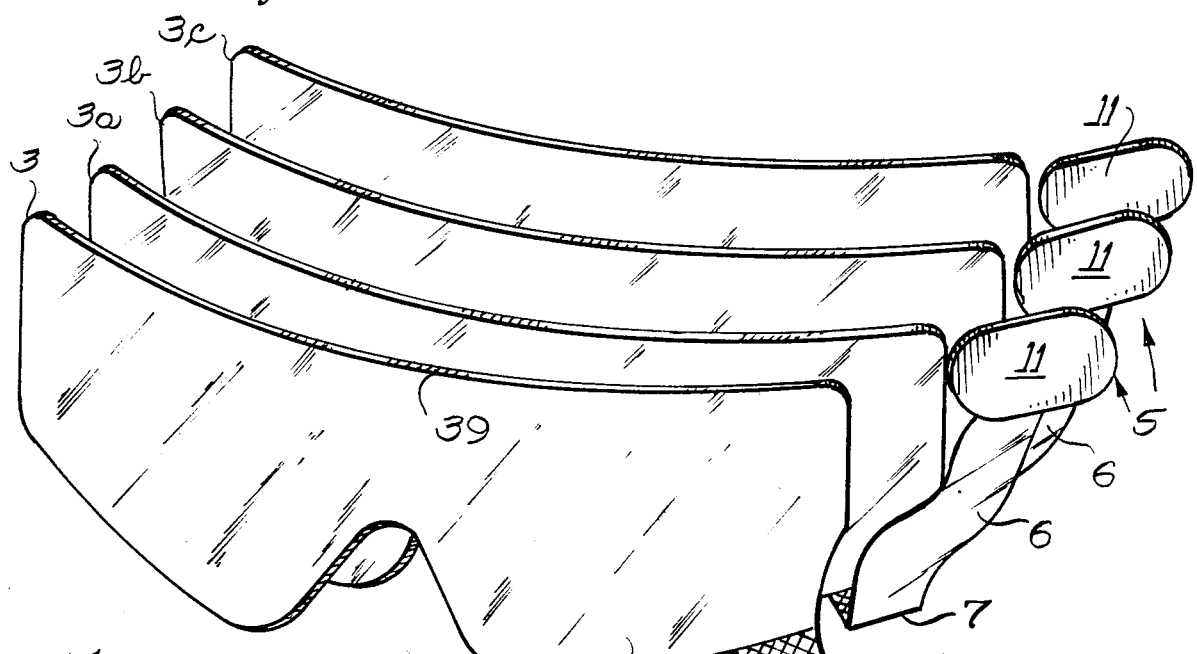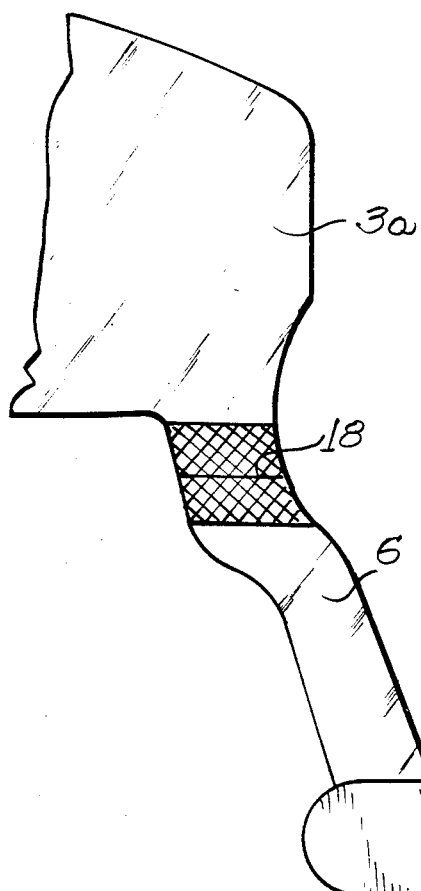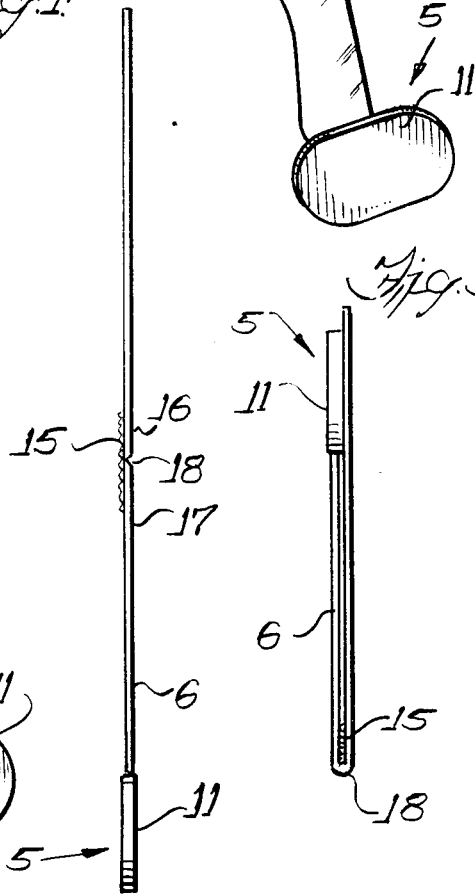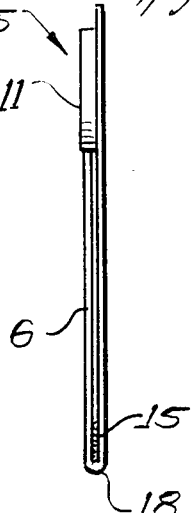

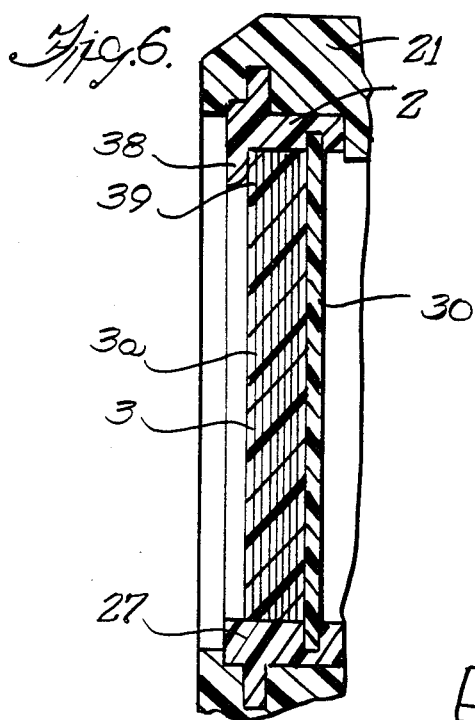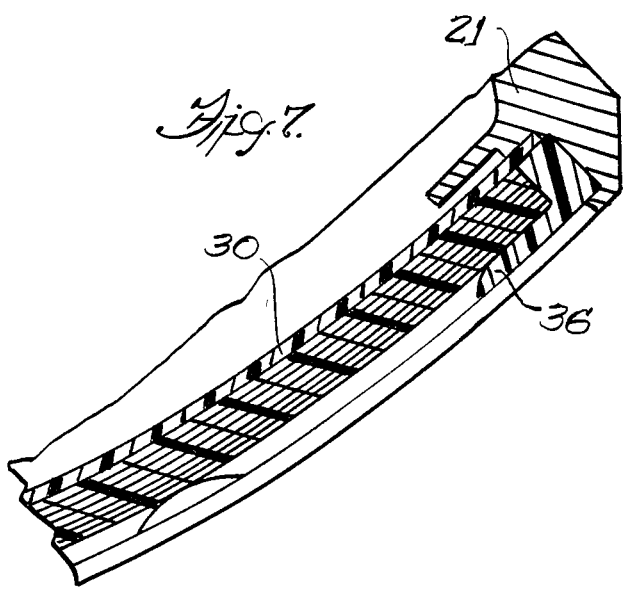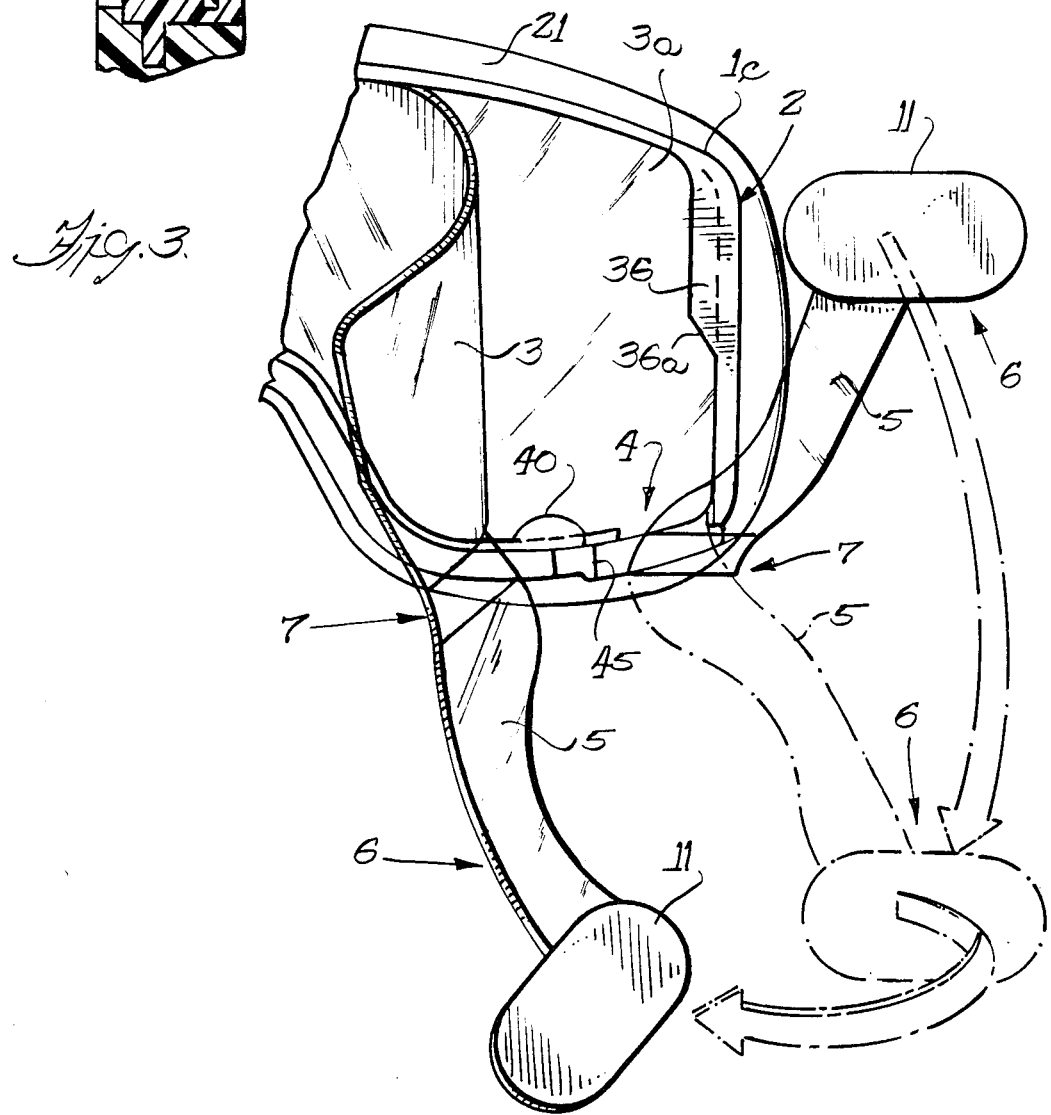

PROTECTIVE GLASSES WITH TEAR-OFF LENSES

BACKGROUND OF THE INVENTION

The present invention concerns a pair of protective glasses which are equipped with tear-off lenses, for example, for motorcycle riders, skiers, etc., whereby a tear-off lens, after it is sprayed in a manner which impedes vision, perhaps by rain water, street dust, snow flakes, etc., is torn off the eyeglass frame and discarded, exposing a tear-off lens lying under it, which again affords the wearer of the eyeglasses clear vision.

Protective eyeglasses of this kind have eyeglass bodies including a frame in which is fixedly mounted a stationary non-removable main lens which is covered by several layers of tear-off lenses. The latter are carried in a frame which extends essentially around the entire inner extent of the eyeglass body and at a certain spacing in front of the main viewing lens. A groove is formed between main viewing lens and frame into which groove is inserted several tear-off lenses of flexible, transparent foil, which lie one on top of the other and which correspond to the shape of the main viewing lens.

In a known protective glass, each of the tear-off lenses bear a gripping tab which projects out of a recess of the frame, which tab the eyeglass wearer grasps as needed to tear off a lens. The packet of tear-off lenses are disposed in the groove such that the gripping tabs of the lenses lie one on top of the other and project from the eyeglass body alternatively to the right and to the left. This has the disadvantage that the eyeglass wearer must clearly note whether the previous tear-off lens had its gripping tab on the right or on the left side of the glasses. If this is forgotten, then the eyeglass wearer, when removing the next tear-off lens, will grasp the gripping tab of the second-to-next lens, with the result that then two lenses are torn off at once, and thus one of the lenses is lost without being used.

Also it has been known in protective glasses to displace the tabs of the individual lenses which lie one on top of the other in the manner of a fan. Here there is a danger that the eyeglass wearer when tearing off a lens will grasp two gripping tabs at once and thereby also throw away a further tear-off lens unused.

Thus, there is a need to create a pair of protective glasses with tear-off lenses which no longer have the above-mentioned deficiencies of the previous glasses and which reliably guarantees a consecutive tearing-off of individual lenses.

This need is solved by the present invention which comprises an eyeglass body with a fixed-mounted main viewing lens and a frame extending essentially around the entire inner extent of the eyeglass body and at a certain spacing in front of the main viewing lens and a packet of tear-off lenses with gripping tabs inserted behind this frame, each of the tear-off lenses having gripping tabs attached on the lower edge on one side of the glasses and with a stem having one end connected with the gripping tab and the other end of which is attached foldable by means of a hinge onto the associated tear-off lens, the tabs are disposed with the individual stems folded about their hinges and the stem of one lens is held in this folded-up position by means of the lens lying over it.

An example of the embodiment form of the inventive protective glasses will now be explained more precisely with reference to the attached drawings.

FIG. 1 is a front elevational view of the preferred embodiment of protective glasses embodying the invention;

FIG. 1A is an enlarged fragmentary sectional view taken along line 1A—1A of FIG. 1;

FIG. 1B is an enlarged fragmentary sectional view taken along the 1B—1B of FIG. 1;

FIG. 2 is an exploded view of a tear-off lens packet of the protective glasses for the protective glasses of FIG. 1;

FIG. 2A is a fragmentary view of lens and its tab;

FIG. 3 is a partial view similar to that of FIG. 1 showing the process of the tearing off of the front tear-off lens;

FIG. 4 is a side elevational view of a lens and tab;

FIG. 5 is a side elevational view of a tab in its folded position; and

FIGS. 6 and 7 are enlarged cross-sectional views taken along the lines 6—6 and 7—7, respectively of FIG. 1.

As shown in FIG. 1, the present invention comprises protective glasses having an eyeglass body 1, in which is fixedly mounted a main viewing lens 30 (FIG. 1A and 1B). Mounted in the eyeglass body is a lens carrying a frame 2 which extends essentially around the entire inner extent of the eyeglass body wall 21 and which projects outwardly from a main viewing lens carried inside of the eyeglass body 1. A groove is formed between the main viewing lens and the frame to serve as a receiving pocket for a packet of tear-off lenses. In FIG. 1, only the uppermost, or front tear-off lens can be seen. A packet of tear-off lenses outside of the eyeglass frame 2 is depicted in FIG. 2. Although here, for the sake of simplicity, the packet consists only of the four lenses 3, 3a, 3b and 3c, it is understood that in practice, five, eight or more. It can also be seen in FIG. 2 that the stem 5 with gripping tab 6 of the second tear-off lens 3a which is folded upward about the hinge 7 remains in this position and cannot open up downward, because it is prevented from doing this by means of the surface of the front tear-off lens 3. Since there is no further tear-off lens in front of the front tear-off lens 3, its stem 5 falls down out of the folded-up position. Thus the result, which is also apparent from FIG. 1, is that the stem with the gripping tab 6 of the front tear-off lens hangs down, while the stem 5 with gripping tab 6 of all tear-off lenses lying behind it remain folded up in each case by means of the tear-off lens lying directly before it.

If the eyeglass wearer wants to remove the front, or top tear-off lens 3, then he pulls on the gripping tab 6 which is hanging down. With this, the lens 3a which lies behind, or under it, becomes the front lens, and the impedance which held the stem 5 with gripping tab 6 of the lens 3a in the folded up position is removed. Thus the gripping tab 6 of the lens 3a assumes the same position as had been assumed previously by the gripping tab of the lens 3 which was removed (compare FIG. 3, direction of the drawn-in arrow).

The same process is repeated with the tearing-off of each further lens, so that the eyeglass wearer always finds the gripping tab 6 for removal of the next lens in the same position, to be torn off with the same hand, and thus a simultaneous, unintentionally tearing off of several lenses is completely excluded.

Preferably, the frame 2 in the region of the hinges 7 is provided with a recess or groove 4, into which the hinges are seated. The hinges can consist of flexible polyamide web 15 (FIGS. 3, 4 and 5), which is welded to a depending finger 16 on the tear-off lens edge on the one side and the upper end 17 of the stem on the other side. The stem 5 may be made of the same material as the disposable lens and may be joined thereto at a juncture line 18 which may be a line of reduced cross section (FIG. 4). The hinge may be made so that it has a memory to assist in the tab falling down whenever possible. However, other suitable hinge materials and other fastening techniques can also be employed.

The preferred gripping tab 6 includes a finger grip 11 of a material substantially thicker and heavier than the lens and stem material. This assures that the heavier finger grip 11 will fall down and remain down so as to be easily gripped. To assist in gripping the finger grip, it is made of a flat wide piece extending substantially normal to the stem and in a general horizontal plane. Each finger grip 11 for each lens will drop to substantially the same position for gripping by the wearer who may pull the same while keeping his attention on the endeavor he is engaged in.

The eyeglass body 1 comprises a conventional goggle shaped body having curved lenses therein and is usually mounted on the wearer's head by an adjustable head strap (not shown) which is connected to opposite ends 1c and 1d of the eyeglass body. Typically, the eyeglass body is a molded flexible piece of plastic having a groove 31 (FIGS. 1A, 1B) formed in the molded eyeglass body to receive the frame 2. Herein, the groove 31 is defined between an inner flange 23 and an outer flange 25 which are spaced to receive therebetween the outer peripheral rim 27 of the lens carrying frame 2. In this instance, the lens carrying frame 2 is molded of a more rigid plastic than the plastic of eyeglass body. The permanent lens 30 may be staked or otherwise fixedly secured to the rearward, vertical side 2a of the lens carrying frame, as best seen in FIGS. 1A and 1B.

The groove 41 for receiving the lens packet is herein defined by the rear lens 30 and a pair of side retaining webs 35 and 36 on the lens retaining frame 2. The webs 35 and 36 project inwardly toward the nose piece seen in FIGS. 1 and 1A for a short distance. As best seen in FIGS. 1 and 1a, the retaining web 35 extends the full vertical height of the lens whereas the opposite web 36 only extends upwardly from about the center of the lens at which is an inclined edge 36a. Assisting in holding the lens in the groove is a depending top web 38 which is located at the centerline of the protective glasses. This holds the central upper central part of edges 39, FIG. 2 of the tear-out lenses 3, 3a, 3b and 3c. At the lower right portion of the lenses, as viewed in FIGS. 1 and 3, and adjacent the recess 4 is an upstanding web 40 will engage the lenses at the area 42, as shown in FIG. 2, near a tab-receiving recess 4 (FIG. 1) at which are located the stems 5 of the pull-out lenses of the packet. The recess 4 is formed by a discontinuity or space in the outer lower flange 25 of the eyeglass body between a left hand wall 45 and a right hand wall 46 at the location of the stem 5. Also, a discontinuity in the bottom peripheral rim 27 of the frame 2 at the location of the stems assists in forming the recess 4. The recess 4 is thus formed so that each lens will have its stem 5 hanging substantially straight downwardly.

From the foregoing, it will be seen that a protective glass is formed with hinged pull off tabs that automatically drop into the same general position for each lens as each preceding tear-off lens is removed. The tabs are held in their folded up positions by the immediately preceding lens in the packet and drop automatically as the immediately preceding lens is removed.

What is claimed is:

1. Protective glasses with removable lenses adapted to be torn away when dirty to reveal a new clean lens, said protective glasses comprising:
   an eyeglass body for affixing to the head of the wearer;
   a packet of tear-off lenses stacked for removal from the packet;
   means on the eyeglass body to releasably retain each of the tear-off lenses in operative position to protect the eyes of the wearer,
   gripping tabs connected to each lens at substantially the same location, and
   hinge means for each grippng tab allowing the tab to be folded upwardly about its hinge so as to extend upwardly in a stowed position adjacent one side of the eyeglass body, the lower adjacent edge of the immediately underlying tear-off lens engaging and holding the tab of the immediately underlying lens in an upstanding, stowed position, and means on upper ends of the gripping tabs for causing the outermost tab to fall downwardly and to pivot about its hinge means to an operative downwardly extending grippig position as the lens immediately preceding in the packet is torn from the packet.

2. Protective glasses in accordance with claim 1 in which a main viewing lens is fixedly mounted in the eyeglass body behind the packet of tear-off lenses.

3. Protective glasses in accordance with claim 2 in which the means on the eyeglass body to retain the tear-off lenses comprises a peripherally extending frame extending substantially about the eyeglass body and attached thereto and having portions spaced from said main viewing lens to define a groove to receive edges of the tear-off lenses.

4. Protective glasses in accordance with claim 1 in which the tabs comprise a stem connected at one end to the hinge means, and a finger grip attached to the other end of the stem to be grasped by the wearer when tearing off the lens.

5. Protective glasses comprising:
   an eyeglass body;
   a main viewing lens;
   a frame extending around the inner extent of the eyeglass body and spaced in front of the main viewing lens;
   a packet of tear-off lenses inserted behind the frame and in front of the main viewing lens;
   a gripping tab including a stem on each tear-off lens being attached on the lower edge of its associated lens and on one side of the glasses
   a hinge connecting each tab to its associated tear off lens;
   the individual stems being folded upwardly about their hinges to a stowed position adjacent one side of the eyeglass body with the stem of a lens being held in this folded position by means of the lens lying on top of it, and means on the upper end of the stem of the outermost lens in the packet for falling downwardly and pivoting the stem about its hinge to an operative downwardly extending gripping position hanging downwardly from the eyeglass body.

6. Protective glasses according to claim 5 in which the frame in the region of the hinges of the tear-off lenses is provided with a recess.

7. Protective glasses according to claim 5 in which the hinge includes a polyamide web, which is welded to the edge of the tear-off lens and the end of the stem.

* * * * *

UNITED STATES PATENT AND TRADEMARK OFFICE
CERTIFICATE OF CORRECTION

PATENT NO. : 4,563,065
DATED : January 7, 1986
INVENTOR(S) : Franz Kreissl

It is certified that error appears in the above-identified patent and that said Letters Patent is hereby corrected as shown below:

Column 2, line 10, after "along" delete "the" and insert --line--.

Column 2, lines 37-40, after "practice" insert --such a packet encompasses a larger number of lenses, for example,--.

Column 3, line 19, delete "horizonal" and substitute therefor --horizontal--.

Column 3, line 44, delete "la" and substitute therefor --1A--.

Column 3, line 53, after "web 40" insert --which--.

Column 4, line 24, delete "grippig" and substitute therefor --gripping--.

Column 4, line 50, after "glasses" insert --;--.

Signed and Sealed this

Nineteenth Day of August 1986

[SEAL]

Attest:

DONALD J. QUIGG

Attesting Officer

Commissioner of Patents and Trademarks